United States Patent
Lee

(10) Patent No.: US 6,574,511 B2
(45) Date of Patent: Jun. 3, 2003

(54) PASSIVE DATA COLLECTION SYSTEM FROM A FLEET OF MEDICAL INSTRUMENTS AND IMPLANTABLE DEVICES

(75) Inventor: Michael Thomas Lee, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 42 days.

(21) Appl. No.: 09/838,697

(22) Filed: Apr. 19, 2001

(65) Prior Publication Data

US 2001/0049544 A1 Dec. 6, 2001

Related U.S. Application Data

(60) Provisional application No. 60/198,974, filed on Apr. 21, 2000.

(51) Int. Cl.$^7$ .................................................. A61N 1/36
(52) U.S. Cl. .......................... 607/60; 128/903; 607/32
(58) Field of Search ................................ 607/5, 32, 48, 607/60; 128/903

(56) References Cited

U.S. PATENT DOCUMENTS

| | | | | |
|---|---|---|---|---|
| 4,524,774 A | * | 6/1985 | Hildebrandt | 128/421 |
| 5,481,262 A | * | 1/1996 | Urbas et al. | 128/903 |
| 5,752,976 A | | 5/1998 | Duffin et al. | 607/32 |
| 5,814,089 A | * | 9/1998 | Stokes et al. | 607/32 |
| 6,083,248 A | * | 7/2000 | Thompson | 607/30 |
| 6,141,588 A | * | 10/2000 | Cox et al. | 607/9 |
| 6,185,452 B1 | * | 2/2001 | Schulman et al. | 604/20 |
| 6,272,379 B1 | * | 8/2001 | Fischell et al. | 607/5 |
| 6,386,882 B1 | * | 5/2002 | Linberg | 434/262 |
| 6,424,867 B1 | * | 7/2002 | Snell et al. | 607/31 |
| 6,443,891 B1 | * | 9/2002 | Grevious | 600/302 |

* cited by examiner

Primary Examiner—Carl Layno
(74) Attorney, Agent, or Firm—Girma Wolde-Michael

(57) ABSTRACT

A passive communication scheme between one or more external instruments communicable with one or more implanted medical devices (IMDs) provides a system to collect data from the IMDs. Further, the one or more programmers are communicable with a remote central server or a network where the collected data is stored. The one or more external instruments exchange data by passively interrogating each other and any proximate IMD or IMDs. Specifically, the external instruments may be represented by a programmer type device. The programmer is enabled to interrogate and exchange data with one or more IMDs in one or more patients when they come within telemetry or wireless communication range. Similarly, two or more programmers interrogate and exchange data with each other when placed within a telemetry or wireless communication range. Further, data collected by the programmer or programmers is transferred to a central location using network and equivalent data transmission medium.

19 Claims, 3 Drawing Sheets

PASSIVE DATA COLLECTION SYSTEM FROM A FLEET OF MEDICAL INSTRUMENTS AND IMPLANTABLE DEVICES

This application claims the benefit of provisional application No. 60/198,974 filed on Apr. 21, 2000.

FIELD OF THE INVENTION

The present invention generally relates to implantable medical devices (IMDs) and instruments. Specifically, the invention relates to an apparatus and method that enables exchange of medically relevant data and information between a number of instruments and IMDs. More specifically, the invention pertains to passive data exchange and collection based on a plurality of instruments, which may interrogate each other and/or IMDs for the purpose of exchanging pertinent data. The system is compatible with and may operate within a network or web-enabled system for transferring the passively collected data.

BACKGROUND OF THE INVENTION

After the implantation of an IMD, such as for example, a cardiac pacemaker, clinician involvement with respect to the IMD has typically only begun. The IMD cannot be implanted and forgotten, but must be monitored for appropriate operation. The IMD may also require occasional adjustment of certain parameters or settings to optimize its functionality for therapy and diagnosis. In addition, IMDs may also need to be replaced in response to or in anticipation of changes in patient condition or other environmental factors, or based on factors internal to the device, battery depletion, for example. Instruments that program the IMDs may also require firmware or software upgrades or modifications.

Further, the implantation of a medical device is an event that must be carefully documented or recorded by various clinicians and commercial entities. For example, per FDA requirements, a clinician must record information about the device such as its serial and model number in order to inform the patient of any health safety alerts, should these occur. Such information is also useful if any firmware or software updates or upgrades involving the device are to be made. These same data are necessary if the physician is to issue reminders to the patient regarding significant dates involving the IMD in order to generally aid in patient compliance. The IMD may also require regular maintenance checks, suggested or prescribed. The renewal of a power supply or the refilling of a reservoir containing a drug administered by the device are examples of routine maintenance that may be required. Similarly, the manufacturer and/or seller of the device will probably wish to match information about the device such as its serial and model number, manufacturing date, its batch or lot, with, for example, the patient receiving the implant and/or the clinical entity administering the device. Maintaining such a database ensures that any important information involving the device may be promptly provided to the FDA, the patient, and the clinician either directly or indirectly.

Further, medical practice dictates that an accurate record of past and contemporaneous programming sessions be documented. Typically, such a report identifies all the medical devices involved in any interactive procedure. Specifically, all data collected by peripheral and major instruments that downlink to the IMD may be reported. Currently, such procedures are reported only when the instrument is in direct contact with the IMD via an RF programming head. And while the data accumulated by the IMD may be uplinked to the instrument, some data requires manual entry during each procedure, for example, the model and serial number of the IMD in/on a piece of documentation. One of the limitations of this procedure is the fact that it is error prone and requires rechecking of the data to verify accuracy. The use of human clinicians and technicians to analyze data and document changes in device therapy based on clinical diagnoses also may result in inefficiencies and errors.

Thus, it may be desirable to limit clinician, technician, or other human involvement in documenting certain information about the IMD and its operation within a patient, once the IMD is implanted. For example, after implantation, the IMD must be registered, specifically by model and serial number among other pieces of required data.

There is also a need to monitor the status of the instrument/programmer on a regular, if not continuous, basis to ensure optimal patient care. In the absence of other alternatives, this imposes a great burden on the patient if a hospital or clinic is the only center where the necessary upgrade, follow up, evaluation and adjustment of the IMDs can be made. Further, even if feasible, the situation involving patients with multiple implants would require the establishment of multiple service areas or clinic centers to support the burgeoning number of multi-implant patients worldwide.

A technology-based health care system that fully integrates the technical and social aspects of patient care and therapy should be able to flawlessly connect the client with care providers irrespective of the separation distance or location of the participants. While clinicians will continue to treat patients in accordance with accepted modern medical practice, developments in communications technology are making it ever more possible to provide medical services in a time and place independent manner.

The frequent use of programmers to communicate with the IMD and provide various remote services, have become an important aspect of patient care as indicated in the disclosures contained in co-pending applications titled "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430, 708 "Apparatus and Method for Automated Invoicing of Medical Device Systems," filed Oct. 29, 1999, Ser. No. 09/430,208; "Apparatus and Method for Remote Self-Identification of Components in Medical Device Systems," filed Oct. 29, 1999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No. 09/431,881; "Virtual Remote Monitor, Alert, Diagnostics and Programming For Implantable Medical Device Systems" filed Dec. 17, 1999, Ser. No. 09/466,284; "Integrated Software System For Implantable Medical Device Installation and Management" filed Dec. 24, 1999, Ser. No. 60/173, 082 which are all incorporated herein by reference in their entirety.

In related art, Ferek-Petric discloses a system for communication with a medical device in a co-pending application, Ser. No. 09/348,506 that is incorporated herein by reference in its entirety. The disclosure relates to a system that enables remote communications with a medical device, such as a programmer. One of the significant teachings of Ferek Petric's disclosure, in the context of the present invention, includes the implementation of communication systems, associated with IMDs, that are compatible with the Internet. Specifically the disclosure advances the art of remote communications between a medical instrument, such as a programmer, and experts located at a remote location using the Internet. As indicated in the disclosure, the communications scheme is structured to primarily alert remote experts to existing or impending problems with the programming device so that prudent action, such as early maintenance or other remedial steps, may be timely exercised. Further, because of the early warning or advance knowledge of the problem, the remote expert would be well informed to provide remote advice or guidance to service personnel or operators at the programmer.

Accordingly, there is a need for a system in which a programmer and/or IMD could passively exchange and/or collect device, instrument related data as well as pertinent clinical data, in a secure manner, with a plurality of programmers that are in contact with an Information Network. Specifically, telemetry or equivalent wireless systems could be structured to transmit the data to any other instrument. These data could then be transferred to a remote data center where a physician or other health care specialists can take any necessary action in response to the transferred data. Such actions include but are not limited to: remote analysis of the data, suggested changes to programmed parameters, notification that the IMD has reached elective replacement status, inter alia. As discussed herein below, the present invention provides these and other means to ensure such transfer of data.

SUMMARY OF THE INVENTION

The present invention discloses an apparatus and method by which medical instruments communicate and exchange data autonomously with each other as well as with IMDs in a passive manner. Accordingly, there is no need for any human intervention to initiate the transfer of data.

In this invention, one or more IMDs, such as a pacemaker, defibrillator, drug pump, neurological stimulator, or physiological signal recorder may be deployed in a patient. The IMD is preferably equipped with a radio frequency transmitter or receiver, or an alternate wireless communication telemetry technique or media that enables signals to travel through human tissue. For example, the IMD transmission device might be a radio frequency telemetry, acoustic telemetry, or a transmission technique that uses patient tissue as a transmission medium. Alternately, an IMD may be deployed in a manner by which a transmission or receiving device is worn externally by the patient but is connected directly or via wires to the IMD. An external instrument, generally termed a programmer, is positioned outside the patient. The programmer is also equipped with a radio frequency or other communication means compatible with the communication media of the IMD or the IMD transmitter/receiver. Communication may be effected between the IMD transmitter/receiver and the external programmer, e.g. via radio frequency. The programmer is preferably connected via a wireless or direct connection communication media, such as, for example, a modem and direct dial connection, with a data network, LAN, WAN, wireless, or infrared network. The present invention includes a scheme for enabling communication between programmers at times when they are not in contact with a data network. Subsequently, when one of these programmers, comes into contact with a network, it would "bubble up" data that was previously exchanged between the programmers in a passive manner.

One of the other distinguishing features of this invention includes the use of a highly flexible and adaptable communications scheme to promote real-time communications between a programmer and a plurality of co-implanted medical devices (CIMDs). The CIMDs are structured to share information intracorporeally and may interact with the programmer, as a unit. Specifically, the CIMDs either jointly or severally can be interrogated to implement or extract clinical information as required. In other words, all of the CIMDs may be accessed via one IMD or, alternatively, each one of the CIMDs may be accessed individually. The information collected in this manner may be transferred to the programmer by up linking the IMDs as needed.

In one embodiment of the present invention, instruments/programmers in close proximity with each other could exchange and transfer small files. Such files could be, for example, the form of audit files consisting of very short text files containing model and serial number, software revision number, date and time stamp of the transaction. Subsequently, when either programmer is connected to the main server, termed the Medtronic Information Network (MIN), these audit files are uploaded to the server. These data might reveal, for example, that one of the instrument/programmers did not have the most current software revision. When this information is uploaded to the MIN, the institution who "owns" the instrument will be automatically notified of this fact and advised to have the software updated. Thus, the passive collection of these and subsequent data assists in maintaining compliance with the FDA's traceability standards for medical instruments and IMDs.

In a similar fashion, this passive method of data collection may also be used to upload IMD and patient data through the system and, ultimately, to the MIN, as generally disclosed in U.S. Pat. No. 5,752,976 issued to Duffin, et al., incorporated herein by reference in its entirety. The goal of the complete system is to have IMD and patient data available on one server, with immediate access to physicians and clinicians anytime and anywhere. One of the critical elements is to have all these data resident on the MIN, so that they can be distributed to medical personnel if and when requested. Consistent with the system disclosed in the '976 patent, clinicians may have to alter their accustomed protocol. Compliance may be difficult to some and, as a result, there may be occasions when relevant data is not uploaded to the MIN. In such cases, passive data collection will ensure that such a transfer will ultimately occur. If the patient is at home and is using a home monitoring system, pertinent data not uploaded but relevant to the IMD and/or the patient will be automatically uploaded either transtelephonically or by wireless technology. On the other hand, when the patient visits the clinic, these data may be automatically transferred to the programmer either during device interrogation or by wireless technology, e.g., Blue Tooth, Telemetry C, even if the patient is seated in the waiting room to see another type of physician for a complaint not related to the IMD. The next time the clinic programmer uplinks to the MIN, all passively collected data is uploaded. The number of such data collections that any one programmer/instrument can store is limited only by the instrument's nonvolatile memory size. The server will automatically erase these data from the instrument's memory upon confirmation of successful receipt.

Another application of this passive collection of pertinent data involves "missing" instruments. Occasionally, an instrument may be placed in temporary storage within a medical institution and then its location is forgotten. In one possible scenario, one can imagine the "missing" instrument is located in a storage room behind a door that opens up on a main hallway. In accordance with the present invention, all instruments/programmers include an interogable sleep mode that is activated when the programmer is not directly connected to a power source. Thus when a clinician, physician, or manufacturer's representative is transporting or carrying another instrument along this hallway and passes the storage room. The moving instrument would "discover" the missing instrument in the storage room as it passes along the hallway. All the pertinent data files would be transferred to the moving instrument from which they would be uploaded the next time that instrument is in contact with the MIN. The network software would, in turn, inter alia, notify the institution and Medtronic of the device's approximate location as well as any pertinent need, such as updated software.

In another scenario, one can envision an instrument being transported through an airport by a clinician, physician, or more probably a manufacturer's representative. With the passive data collection feature turned on, that instrument might perform a passive data collection transaction with a traveling patient's IMD. These data might include the previously mentioned simple audit file along with more important information, for example, the date and time that an unreported elective replacement indicator (ERI) was tripped. Again, the next time this instrument is in contact with the MIN, these data would be uploaded to the server. The server's software, in turn, would be scanning for pertinent data such as the ERI and, if located, send the patient's physician notification of that fact. Patient data, however, would be encrypted to protect the patient's privacy.

The apparatus and method disclosed in the present invention should not be thought of as limited by the data transfer rate of currently available wireless technology. As technology advances and wireless transmission rates such as for example, the use of broad band, increase this same passive data collection method will allow the transfer of very large amounts of data.

The present invention will now be described with reference to the following drawings, in which like reference numbers denote the same element throughout.

DETAILED DESCRIPTION OF THE DRAWINGS

Figure 1:
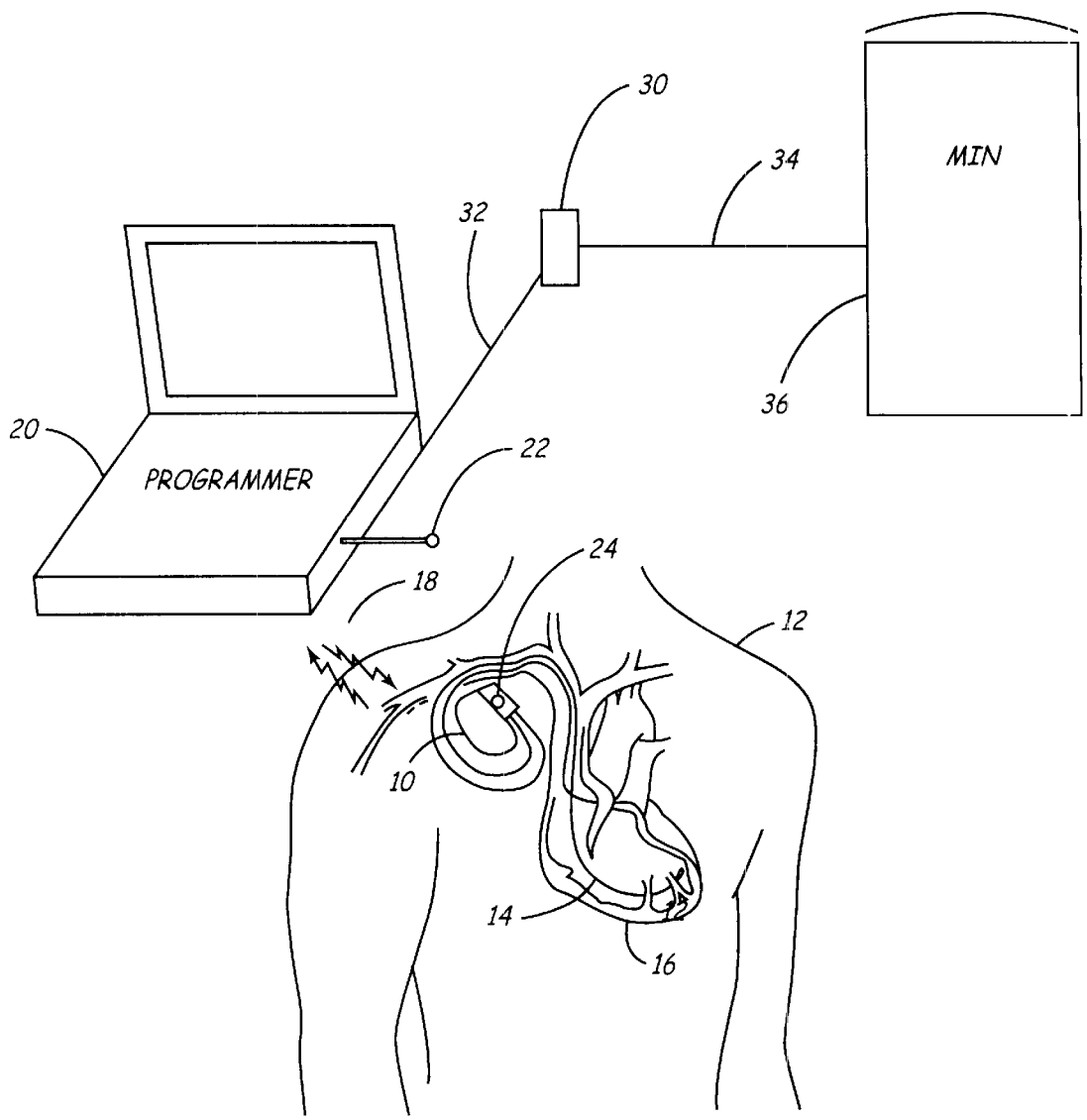
FIG. 1 is a simplified schematic diagram of the major uplink and downlink telemetry communications between the remote server, a programmer and an implantable medical device (IMD).

FIG. 1 is a simplified schematic of the major components of the present invention. Specifically, bi-directional wireless communications 18 between programmer 20 and implanted IMD 10 is shown. IMD 10 is implanted in patient 12 beneath the skin or muscle. IMD 10 contains a microprocessor for timing, sensing and pacing functions consistent with preset programmed functions. IMD 10, in this illustration, is a pacemaker with lead(s) 14 implanted in heart 16 to carry pacing pulses to heart 16 and cardiac depolarization signals from heart 16 to sensing circuitry of IMD 10. Communication between programmer 20 and IMD 10 is coordinated preferably using wireless telemetry communications 18. Programmer 20 may transmit commands to or receive data from IMD 10 via external RF telemetry antenna 22. In a similar fashion, IMD 10 may transmit data and received commands via telemetry antenna 24. RF telemetry antenna 22 may be located on programmer 20 externally on its casing or housing. Telemetry antenna 22 is either adjustable or generally telescoping and may be adjustable on the casing of programmer 20. In the context of the present invention, programmer 20 may pass or be located proximate within 20–30 feet from patient 12 and still be within range to wirelessly communicate with programmer's RF telemetry antenna 22 via IMD's telemetry antenna 24.

The uplink of data to MIN 36 is accomplished via programmer 20. There are a variety of wireless media through which data communications could be established between programmer 20 and MIN 28. In the context of the present invention, the communications link between programmer 20 and MIN 36 will typically be modem 30, which is connected to programmer 20 by line 32 and to MIN 36 by line 34. Alternate data transmission systems include, without limitations, stationary microwave and/or RF antennas, mobile systems, and satellite.

Functionally, programmer 20 with passive data collection feature activated could pass or be located within 20–30 feet of patient 12. Under this scenario, programmer 20 contacts IMD 10 via antenna 22, or IMD 10 contacts programmer 20 via antenna 24. At this point, an exchange of small audit files containing data, for example, as device model number, serial number, might take place.

In other embodiments, patient 12, rather than having only one IMD 10, might have several IMDs, which would communicate with each other. Ultimately one of the IMDs would function as the primary communicator with programmer 20 to uplink the various data from all the IMDs.

Figure 2:
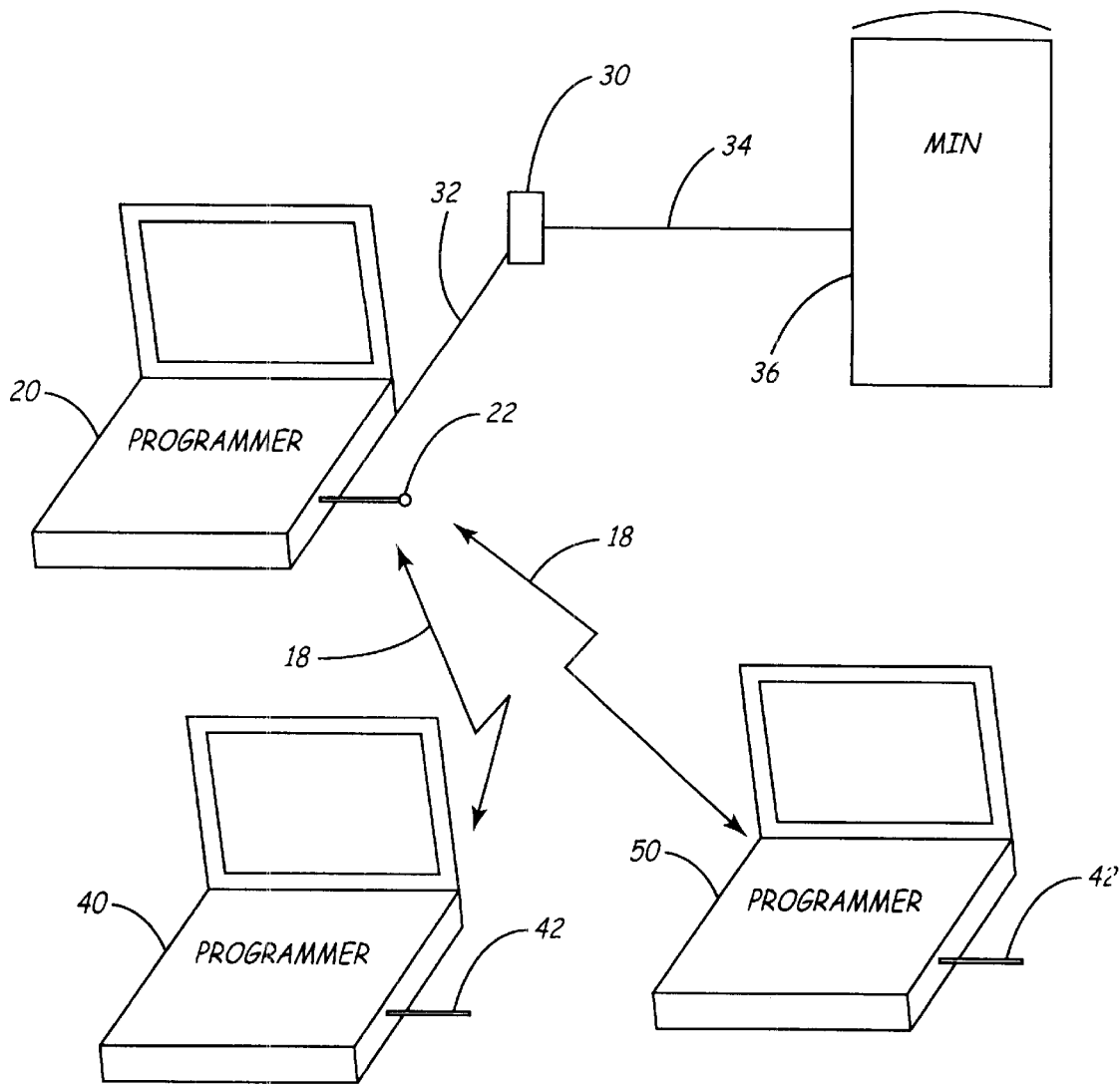
FIG. 2 is a simplified schematic diagram of the telemetry communications between the remote server, a programmer, and other programmer(s).

FIG. 2 is a simplified schematic diagram of the telemetry communications between the remote server, a programmer, and other programmer(s). Additionally, rather than programmer 20 communicating with IMD 10, programmer 20 can exchange data in a passive manner with a second, third, or more programmer(s).

Referring to FIG. 2 in more detail, programmer 20 may passively uplink data from programmer 40 and/or programmer 50. Programmer 40 with wireless antenna 42 may be located in a hospital and, for one reason or other, could be misplaced. As programmer 20 with its passive data acquisition feature activated is transported or carried down a hallway within some 30 feet of programmer 40, programmer 20 "contacts" programmer 40. Wireless telemetry exchanges 18 occur during uplink/downlink of data from programmer 40 to programmer 20. Pertinent data as to the location of programmer 40, as well as, for example, the status of its current software are thus contemporaneously transferred and are recorded in the memory of programmer 20.

The uplink of data to MIN 36 is accomplished via programmer 20. There are a variety of wireless media through which data communications could be established between programmer 20 and MIN 36. In the context of the present invention, the communications link between programmer 20 and MIN 36 will typically be modem 30, which is connected to programmer 20 by line 32 and to MIN 36 by line 34. Alternate data transmission systems include, without limitations, stationary microwave and/or RF antennas, mobile systems, and satellite. Communication with programmer 20 may also take place between a plurality of programmers as is further depicted in FIG. 2. Thus, programmer 20 may passively uplink data from programmers 40 and 50. Assuming programmers 40 and 50 have not been in contact with MIN, their data may be uplinked to programmer 20. Data, representing several programming sessions from a plurality of patients, may then be transferred from programmer 20 to MIN 36 via modem 30 as stated previously. The number of data acquisitions and their volume is limited only by the memory capacity of programmer 20.

Figure 3:
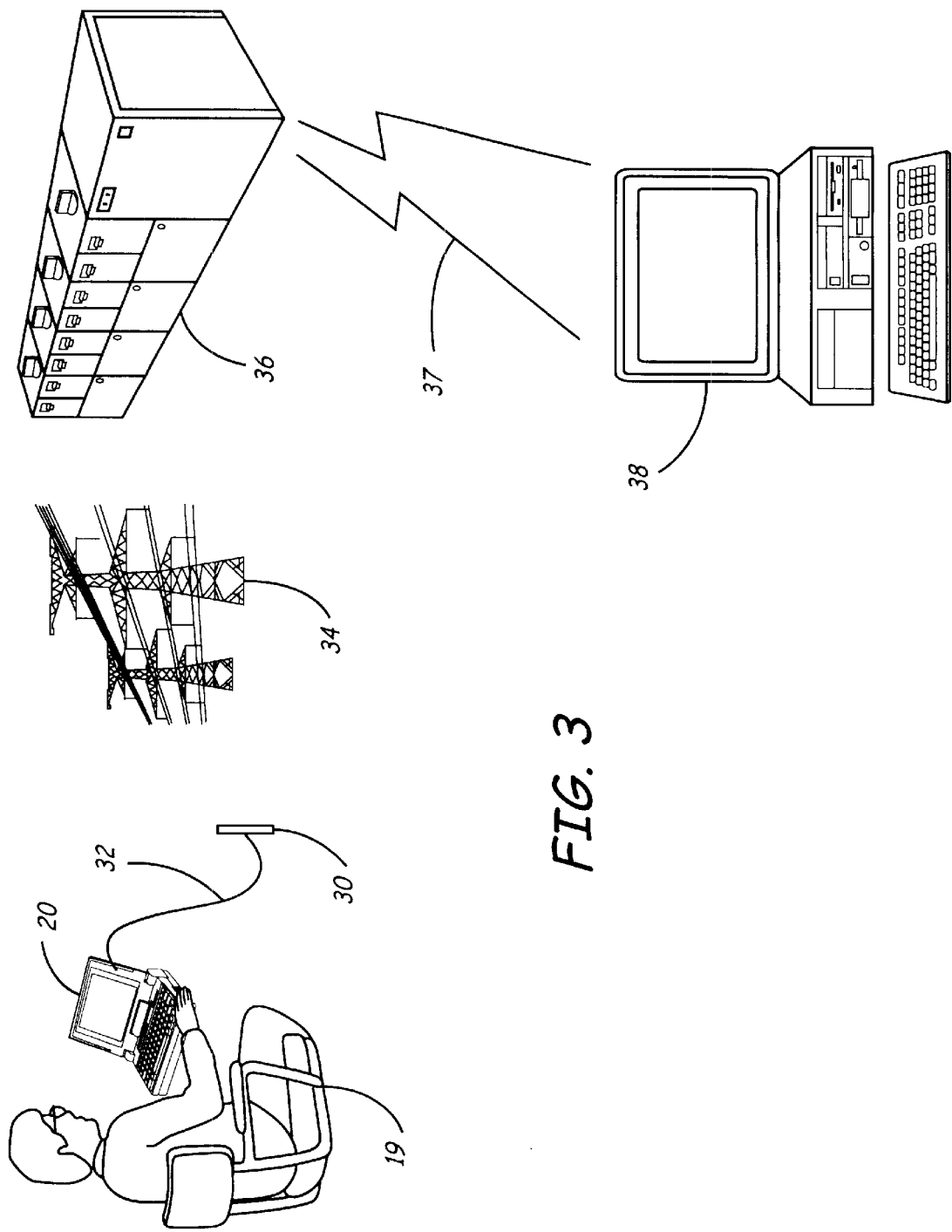
FIG. 3 is a simplified schematic diagram illustrating uplink to the information network and downlink to a clinician's server.

FIG. 3 is a schematic diagram of one embodiment by which the data collected by programmer 20 may be uplinked to MIN 36. In one scenario, manufacturer's representative 19 contacts MIN 36 via programmer 20, connected to modem 30 via wire connection 32. In this scenario, data is transferred via modem 30 to transmission lines 34, Internet, telemetry, or equivalent. Upon receipt of data at MIN 36, client software scans the data to locate clinically critical data such as alerts, significant events, and the like. When critical data is found, the system downloads these data for review by the physician/clinician at server 38. The physician/clinician, when next using server 38, will be advised of alerts and/or significant events, such as the triggering of an elective replacement indicator in an individual patient under the care of the physician/clinician. Physician/clinician may then contact the patient to come into the clinic for a checkup and/or replacement procedure. Non-critical medical/clinical data will be allocated into the appropriate files, by MIN 36 for access by, for example, the physician/clinician, medical institution, manufacturer, and the like, be needed.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A data exchange and transmission system wherein one or more external instruments communicate with each other and with one or more implantable medical devices (IMDs), the system comprising:
   at least two programmers;
   at least one IMD; and
   a wireless communication between said at least two programmers and said at least one IMD;
   said wireless communication upon activation enabling said at least one programmer to passively collect data or transmit data between said at least two programmers and said at least one IMD.

2. The system of claim 1 further comprising a network of one or more programmers adapted to passively interrogate and exchange data between themselves.

3. The system of claim 2 wherein said network of one or more programmers passively interrogates said one or more IMDs.

4. The system of claim 1 wherein said at least two programmers includes a sleep mode that enables communication between said at least two programmers.

5. The system of claim 1 wherein said data is ultimately transferred to a server.

6. A communication scheme between at least two programmers to passively exchange data gathered from one or more IMDs, the communication scheme comprising:
   the at least two programmers;
   a wireless communication scheme; and
   means for passively activating the at least two programmers to exchange the data via said wireless communication.

7. The communication scheme of claim 6 wherein the at least two programmers include a sleep mode wherein sufficient power to sustain said wireless communication means is maintained.

8. The communication scheme of claim 6 wherein said means for passively activating includes a continuous interrogation means between the devices to transfer the data therebetween.

9. The communication scheme of claim 6 wherein said wireless communication means includes a one of telemetry, laser and Blue Tooth.

10. The communication scheme of claim 6 wherein said at lest two programmers interrogate and exchange said data therebetween contemporaneous with acquisition of additional data from said one or more IMDs.

11. The communication scheme of claim 6 wherein said at least two programmers interrogate one another to gather data from each other wherein one of said at least two programmer is misplaced and its location is unknown.

12. The communication scheme of claim 6 wherein said data resident in said at least two programmers is transmitted to a server.

13. A method of gathering data from one or more IMDs, using a passive interrogation scheme implemented in at least one programmer, the method comprising:
   providing the one or more IMDs;
   providing the at least one programmer, and
   enabling a passive wireless communication between said one or more IMDs and the at least one programmer;
   wherein said at least one programmer is provided with a sleep mode power source to continuously and passively interrogate the one or more IMDs and one or more programmers within a range of said wireless communication.

14. The method of claim 13 wherein a plurality of programmers exchange data via said passive wireless communication.

15. The method of claim 13, further comprising providing a plurality of additional programmers and exchanging data between said plurality of additional programmers via passive wireless communication.

16. The method of claim 13 wherein said at least one programmer is implanted to update software resident in said one or more IMDs after precisely checking a resident software in said one or more IMDs.

17. The method of claim 13, further comprising providing a network of programmers and wherein said at least one programmer communicates with said network of programmers.

18. The method of claim 13, wherein said at least one programmer communicates with one or more nomad programmers encountered at random.

19. The method of claim 13, wherein said at least one programmer communicates with one or more nomad IMDs encountered at random.

* * * * *